United States Patent
Cecchetti et al.

(10) Patent No.: US 8,409,176 B2
(45) Date of Patent: Apr. 2, 2013

(54) METHOD AND DEVICE FOR LASER LITHOTRIPSY

(75) Inventors: Walter Cecchetti, Saonara (IT); Wolfgang Neuberger, Labuan (MY); Leonardo Cecchetti, Saonara (IT)

(73) Assignee: Biolitec Pharma Marketing Ltd, Labuan (MY)

( * ) Notice: Subject to any disclaimer, the term of this patent is extended or adjusted under 35 U.S.C. 154(b) by 579 days.

(21) Appl. No.: 12/628,634

(22) Filed: Dec. 1, 2009

(65) Prior Publication Data
US 2010/0137847 A1    Jun. 3, 2010

Related U.S. Application Data

(60) Provisional application No. 61/119,190, filed on Dec. 2, 2008.

(51) Int. Cl.
    *A61B 17/22*      (2006.01)
(52) U.S. Cl. .................. 606/2.5; 606/2; 607/89; 607/93
(58) Field of Classification Search .................. 606/2.5, 606/2; 607/89, 93
See application file for complete search history.

(56) References Cited

U.S. PATENT DOCUMENTS

| | | | |
|---|---|---|---|
| 6,726,681 B2 * | 4/2004 | Grasso et al. ............... 606/15 |
| 6,953,458 B2 * | 10/2005 | Loeb ............................ 606/15 |
| 2002/0030884 A1 * | 3/2002 | Engelhardt et al. .......... 359/385 |
| 2002/0103477 A1 * | 8/2002 | Grasso et al. ............... 606/2 |
| 2006/0122581 A1 * | 6/2006 | Ein-Gal ....................... 606/2 |
| 2009/0299441 A1 * | 12/2009 | Bornstein .................... 607/89 |
| 2010/0179523 A1 * | 7/2010 | Neuberger et al. .......... 606/14 |

* cited by examiner

*Primary Examiner* — Kinam Park
(74) *Attorney, Agent, or Firm* — BJ Associates; Bolesh J. Skutnik

(57) ABSTRACT

A system/method for destruction/ablation of stones, calculi or other hard substances using laser is disclosed. Lithotripsy is particularly benefitted. The system comprises a diode laser source, one or more optical fibers and a liquid delivery system creating a liquid environment around stones (calculi). At least one emitted wavelength is highly absorbed in surrounding/covering medium, causing evaporation and cavitation effects that lead to stone/calculi destruction. Different radiation configurations may be used. in one embodiment continuous radiation is used to create sparkler-less plasma bubbles to destroy hard substances. In another embodiment high peak power pulsed radiation is used. Wavelengths of 1470 nm, 1940 nm, or 1550 nm are preferred. Additionally device/method is used with another wavelength having absorption in water e.g. 980 nm. Safer/improved methods/system provide enhanced lithotripsy treatments with shorter treatment times to destroy a wider range of stones with less tissue damage risk.

13 Claims, 3 Drawing Sheets

METHOD AND DEVICE FOR LASER LITHOTRIPSY

1. DOMESTIC PRIORITY UNDER 35 USC 119(e)

This application claims the benefit and priority of U.S. Provisional Application Ser. No. 61/119,190 filed Dec. 2, 2008, entitled "Method and Device for Laser Lithotripsy" by Leonardo Cecchetti, Walter Cecchetti, and Wolfgang Neuberger, which is incorporated by reference herein.

BACKGROUND OF THE INVENTION

1. Field of the invention

The present invention is related to minimally invasive devices and methods used in laser treatments. More particularly, the invention relates to lithotripsy techniques based on laser radiation.

2. Invention Disclosure Statement

Calculi or stones are the result of a concretion of material, usually mineral salts that form in an organ or duct of the body. They cause a number of important medical conditions by several mechanisms:

Irritation of nearby tissues, causing pain, swelling, and inflammation.

Obstruction of an opening or duct, interfering with normal flow and disrupting the function of the organ in question.

Predisposition to infection due to disruption of normal flow.

The most common types are kidney stones, also called renal calculi, which are present within the urinary tract, mainly the kidneys or bladder and gallstones which develop in the gallbladder.

There are several approaches used in medicine for treating stones. Many calculi in the upper urinary tract are treated with extracorporeal shock-wave lithotripsy (ESWL). ESWL attempts to break up the stone by using an externally-applied, focused, high-intensity mechanical (acoustic) pulse. Extracorporeal lithotripsy works best with stones of small diameter. For those stones that are poor candidates for this modality, endoscopic therapy is indicated. Endoscopic lithotripsy refers to the visualization of a calculus and the simultaneous application of a form of energy to fragment a stone into either extractable or passable pieces. Ureteroscopy is the most common means of visualizing an upper urinary tract calculus. Alternatively, percutaneous techniques also can be used on kidney stones.

Energy sources used in Endoscopic lithotripters include ultrasonic, electrohydraulic, and mechanical devices, as well as various lasers.

Laser lithotripsy was first introduced commercially in the late 1980s, based on the fact that pulsed light energy, delivered via an optical fiber, is converted into mechanical energy in the form of a cavitation bubble associated with the occurrence of shock-waves. This mechanical energy is responsible for the destruction of calculi. It is a procedure underpinned by plasma formation on the surface of stones to be shattered. Through very thin optical fibers, laser impulses are transmitted to the stone surface with high peak power radiation. If stones or the surrounding liquid absorb the radiation and the power density exceeds a certain threshold, plasma formation occurs. The plasma, created by an ionization with rapid growth of the matter, produces sparkler bubbles associated with cavitation and the shock waves effect. The plasma and cavitation phenomena are associated with strong photo and thermo-ablative effects; plasma bubbles have inside temperatures of several thousand of degrees, and the presence of cavitation effects is associated with a typical noise produced by the shock waves.

First laser used was a pulsed-dye laser, emitting at 504 nm of light delivered through optical quartz fibers. This was a nonthermal laser that produced plasma between the tip of the fiber and the calculus, fragmenting stone with a photo acoustic effect. As an example, in U.S. Pat. No. 5,071,422, Watson et al. disclose a method to treat calculi, stones and calcified tissue with a pulsed-dye laser. But if dye laser radiation is not absorbed by stones, plasma formation will not occur and laser lithotripsy will not be effective. Since a pulsed dye laser source is used, frequent maintenance is often required as this source is not a solid-state laser.

As an alternative, Alexandrite lasers have been used for lithotripsy, emitting with very short pulse duration. For instance, in U.S. Pat. No. 5,009,658, Damgaard-Iversen et al. disclose a dual frequency laser lithotripter, which emits at two different wavelengths obtained from an Alexandrite laser. The usage of this kind of lasers has rendered poor results due to the unfavorable absorption at its wavelength range.

Nd:YAG lasers have been used obtaining some good results. As an example, in U.S. Pat. No. 4,960,108, Reichel uses a metal compound rinsing liquid, which is delivered around the target stone and irradiated with a Nd:YAG laser. However, this technology lacks precision compared to other laser technologies. With the need to use high peak powers, another drawback is that the distal end of the fiber may be damaged if it makes contact with the stone.

In an attempt to overcome some of these disadvantages, holmium:YAG lasers emerged, which are thermal lasers using 2150 nm wavelength. The energy is delivered through low-water density quartz fibers. For example, Hoang discloses in U.S. Pat. No. 5,860,972 a method for detection and destruction of urinary calculi using a Ho:YAG laser. These lasers have more precision and are more effective than previously mentioned technologies. However, one important drawback of this laser is that the energy produced has equally powerful effects on stones and soft tissues. Furthermore, size and cost are important issues to take into account. Diode lasers have numerous advantages over ionic crystal lasers. Among them, higher output, at reduced dimensions and weight. They also have simpler and smaller air cooling systems. Moreover, being integrated with optical fibers, they have a high reliability and do not need alignment.

When applying previous state of the art laser lithotripsy techniques, the successive shock wave pressure pulses result in direct shearing forces, as well as cavitation bubbles surrounding the stone, which fragment the stones into smaller pieces that then can easily pass through the ureters or the cystic duct. The process may take about an hour. This can be tiresome and stressful for both physician and patient. Present invention can successfully fragment stones more effectively therefore reducing the duration of the intervention.

Due to the disadvantages and deficiencies of current lithotripsy techniques, a need exists for a device that provides a fast, safe and more economical alternative to address their shortcomings.

OBJECTIVES AND BRIEF SUMMARY OF THE INVENTION

It is an objective of the present invention to provide safer and more effective method and device for the destruction/ablation of calculi or other hard substances.

It is an objective of the present invention to provide safer and more effective method and device for lithotripsy treatment.

It is also an objective of the present invention to provide a laser device comprising combined or single emission of wavelengths, with at least one of them highly absorbed in the medium surrounding/covering the calculi or hard substances, to create evaporation and cavitations to destroy stones.

It is another objective of the present invention to provide faster and more precise method for lithotripsy treatment by means of using multiple optical fibers and one or more wavelengths.

It is yet another objective of the present invention to provide a safer method for lithotripsy which diminishes surrounding tissue damage by means of limiting thermal heating of the stone.

It is yet another objective of the present invention to provide safer and improved method and device through which enhanced lithotripsy treatments can be performed in a shorter treatment time, destroying a wider range of stones with less risk of tissue damage, and less physician and patient stress.

Briefly stated, the present invention provides a system and method for the destruction/ablation of stones, calculi or other hard substances by means of laser energy As a consequence, several important medical treatments can be performed, especially lithotripsy. The system comprises a diode laser source emitting at least at one wavelength, one or more optical fibers which convey laser radiation to the treatment site and a liquid delivery system used for creating a liquid environment around the stones (calculi). The laser device emits at least one wavelength which is highly absorbed in the surrounding/covering medium, thus causing evaporation and cavitation effects that lead to stone/calculi destruction. Different radiation configurations may be used. In one embodiment continuous radiation is used to create sparkler-less plasma bubbles able to destroy hard substances. In another embodiment high peak power pulsed radiation is used. Wavelengths of 1470 nm, 1940 nm, or 1550 nm are preferred. Additionally it can be applied in combination with another wavelength with medium absorption in water such as 980 nm. In another embodiment a concentric double core fiber is used, in which the ignition radiation is guided in near single mode, inner core and the radiation used to maintain and enhance the pulse is guided into the surrounding second outer core. In another preferred embodiment, the use of multiple optical fibers allows for treating larger stones in a shorter time period. In another preferred embodiment, cooling liquid is supplied to the impact site to further reduce thermal heating of the stone, thus diminishing risks of tissue damage caused by stone fragment anchorage and thermal energy. With these safer and improved methods and system, enhanced lithotripsy treatments can be performed in a shorter treatment time, destroying a wider range of stones with less risk of tissue damage, and less patient and physician stress.

The above, and other objects, features and advantages of the present invention will become apparent from the following description read in conjunction with the accompanying drawings.

DETAILED DESCRIPTION OF PREFERRED EMBODIMENTS

Figure 1:
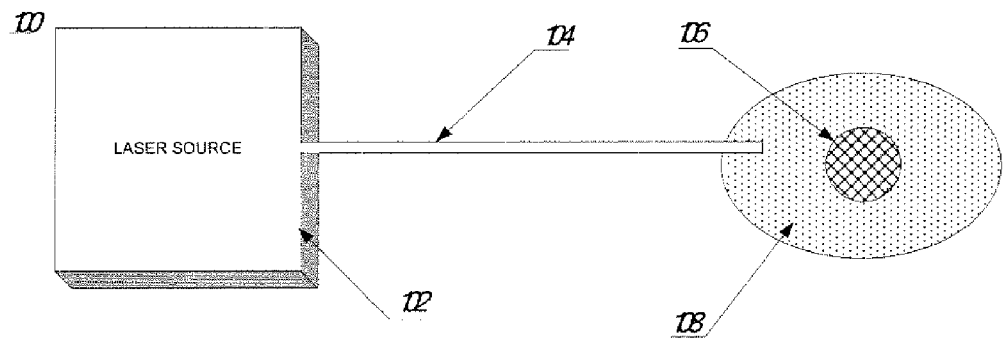
FIG. 1 depicts a preferred embodiment of the present invention in which a lithotripsy treatment device comprises a laser source and an optical fiber.

The prior art techniques' limitations and problems can be overcome, as described in this invention, by a laser lithotripsy technique, which utilizes laser energy coming from one or more diode laser sources to create ablation and cavitations to destroy stones, in a liquid environment. This technique, as explained further below, presents some important advantages compared to previous methods, i.e., shorter treatment time, destruction of a wider range of stones, less risk of tissue damage, and less physician and patient stress. It is also worth mentioning that this technology is not limited to kidney and gallbladder stones, but it may be used for the destruction of any deposits in biological materials, tissues, blood vessels or body cavities since, as mentioned previously, thermal damage of surrounding tissue is minimal. Effective stone fracture is achieved preferably using continuous wave laser sources, thus disclosing a novel treatment conception. As a consequence, a thermo ablation effect with high energy is produced, being capable of shattering calculi of medium hardness.

The present invention discloses an improved method and device for safe and efficient destruction/ablation of calculi (lithotripsy) or other hard substances. The device comprises a diode laser source emitting at least at one wavelength, one or more optical fibers which convey laser radiation to the treatment site and a liquid delivery system used for creating a liquid environment around stones. The laser device emits at least one wavelength highly absorbed in the delivered liquid, preferably in a continuous wave mode, to cause ablation and cavitation effects thus leading to stone destruction.

When highly absorbed radiation is applied to an aqueous medium, water molecules are highly and rapidly heated. This extremely high and immediate heating causes a rapid vapor expansion producing a plasma bubble, which collapses a few millimeters away and after a few milliseconds, producing a crackling noise. Successively, after another few milliseconds, the process repeats and a crackling noise can be heard, which is produced by the bubbles' growth and collapse. These bubbles reach an interior temperature of over a thousand degrees. As a consequence, they have a considerable thermo-ablative effect and also release their thermal energy in the surrounding water. When using a diode laser emitting at 1470 nm in continuous mode, as preferred parameters, fiber tip immersed in liquid medium creates high energy bubbles, which were observed, after investigation, to be plasma bubbles. These plasma bubbles present occasional sparks (always present when using Ho:YAG lasers with short pulses, T<350 μsec), so we call them "sparkler-less" or "sparkless"

plasma bubbles. These sparkler-less plasma bubbles produce a high photothermal effect on the stones with minimal photomechanical effect.

As a consequence, plasma bubbles can be created by using continuous wave sources, being able to produce a thermo-ablation effect with high energy. This is a novel conception when compared to the efforts described in the prior art, which only discloses pulsed laser sources.

Schematically, FIG. 1 depicts a preferred embodiment in which lithotripsy treatment system 100 comprises laser source 102 and optical fiber 104. Optical fiber 104 is positioned near to stone/hard substance 106, which is to be fractured. Optical fiber position can be assessed by means of ultrasound or endoscopy units. Once in position, proximal end of optical fiber 104 is connected to laser source 102, whose radiation is conveyed by optical fiber 104 to the treatment site. Laser source 102 emits at least one wavelength highly absorbed in the liquid 108 surrounding/covering stone/hard substance 106, thus causing evaporation and cavitation effects that lead to stone 106 destruction. Preferably, continuous wave radiation is used to enhance cavitation effects.

Figure 2:
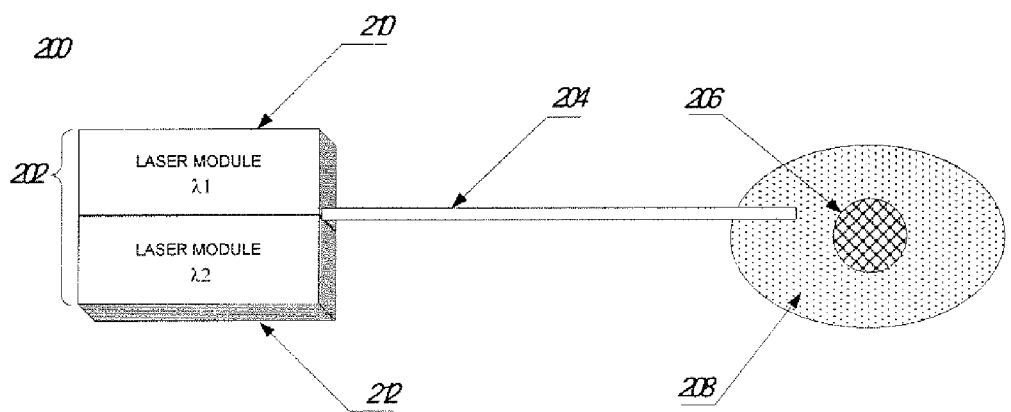
FIG. 2 shows a preferred embodiment of the present invention in which a lithotripsy treatment device consists of a laser source comprising two modules emitting at two different wavelengths.

FIG. 2 shows another preferred embodiment of the present invention in which lithotripsy treatment system 200 consists of laser source 202, which in turn comprises two different modules emitting at two different wavelengths. Module 210 emits at a wavelength $\lambda_1$ highly absorbed in liquid 208 surrounding/covering stone/hard substance 206, thus causing ablation and cavitation effects that lead to stone 206 destruction. Module 212 emits at any useful wavelength $\lambda_2$, in order to enhance or complement the effect caused by module 210. For instance, wavelength $\lambda_2$ can be 980 nm, which has effective enhancing hemostatic effects. According to this concept, more than two modules emitting at different wavelengths can be implemented, thus taking advantage of each of their specific properties.

As an example, clinical trials and vitro tests with histological results using a prototype of present invention (the COMBO laser) can be mentioned which have proven the efficacy of combining two wavelengths for achieving effective sparkless plasma formation for desired tissue effects, particularly 1470 nm and 980 nm diode lasers. When the 1470 nm wavelength is delivered by a thin optical fiber immersed in water, it produces sparkless plasma bubbles with threshold levels as low as 2w of emitted power in a 600 um core fiber. The plasma produced by 1470 nm is able to produce a fast ablation of soft tissue with thin coagulation as well as rupture of hard tissue. The 980 nm wavelength has excellent absorption in blood and less absorption in water. It can produce tissue vaporization associated with a haemostatic effect with a clear whitening. Penetration on tissue is about 2-3 mm. With the COMBO laser, the 1470 nm wavelength produces a plasma bubble on the fiber tip immersed in water. When a simultaneous emission of 980 nm wavelength in the same fiber, arrives into the plasma bubble, it is absorbed at around 70% and the residual 30% exits plasma bubble. Consequently, 70% of the 980 nm energy is converted into plasma, and 70% of this wavelength works as a pump for the plasma bubble produced by the 1470 nm wavelength. The residual 30%, of the 980 nm, reaches the tissue and can produce further homeostasis. Exemplifying this further, with the COMBO laser emitting at a power of 100 W, 75 W were measured at 980 nm and 29 W were measured at 1470 nm. When 100 W were delivered with the fiber immersed in water, plasma bubbles were generated on fiber tip and measurements were 16 W at 980 nm residual out of the plasma bubble. The power supply of the plasma bubbles is 70% of 980 nm, which is around 60 W and 28 W at 1470 nm. Consequently, the plasma bubble is pumped by the two radiations (980+ 1470 nm), and the residual radiation at 980 nm, can work overlapping the plasma bubble to improve the haemostatic effect.

Clinical and in vitro tests thus show that with low power of 1470 nm wavelength, a plasma bubble can be generated, and with the 980 nm wavelength, which has a lower cost and higher efficiency, amplification and growth of this plasma bubble can be achieved.

Additional tests have shown that with the COMBO laser, using 1000 um conical fibers and a power of 120 W, measurements were 35 W at 1470 nm and 93 W at 980 nm.

Figure 3:
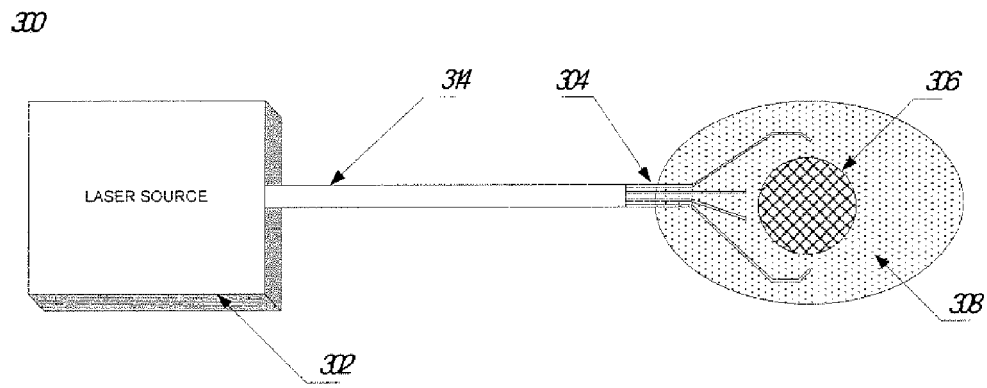
FIG. 3 schematizes a preferred embodiment of the present invention showing a lithotripsy treatment device which consists of a laser source and an optical fiber set comprising multiple optical fibers.

In another preferred embodiment, other combinations of laser sources can be used to achieve diode pumped laser device to generate plasma utilizing plasma ignition means and pulse energizing means. For instance, a double core fiber in which the ignition radiation is guided in the single mode core and the radiation used to maintain and enhance the pulse is guided into the surrounding second core. The single mode or near single mode radiation comes from a fiber laser at 1550 nm diode pumped or a q-switched and the fiber elongated pulse of a diode pumped green laser, and radiation for pulse maintenance and enhancement, which is the major part of the energy would come from a diode laser. The 1550 nm pulses can be generated from 915-980 or 1480 laser diode pumps FIG. 3 depicts another preferred embodiment of the present invention, namely, lithotripsy treatment system 300 comprising laser source 302 with optical fiber set 314 connected. Optical fiber set 314, comprising multiple optical fibers 304, is positioned near to the stone/hard substance to be fractured 306. Each optical fiber 304 of optical fiber set 314 is placed surrounding stone/hard substance 306, in order to impinge on target laser radiation from multiple sites thus leading to efficient stone fracture. This configuration is efficient when trying to destroy larger stones in a shorter time period, for which one optical fiber could be insufficient. Laser source 302 emits at least one wavelength highly absorbed in liquid 308 surrounding/covering stone/hard substance 306, thus causing evaporation and cavitation effects that lead to stone/hard substance 306 destruction.

Figure 4:
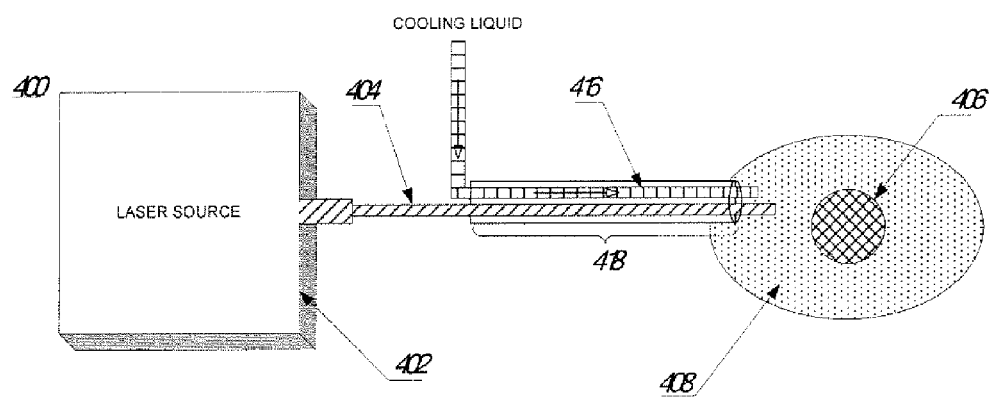
FIG. 4 shows a schematic diagram of a preferred embodiment of this invention in which a lithotripsy treatment device comprises a laser radiation source, an optical fiber and a cooling liquid delivery system.

FIG. 4 shows another preferred embodiment of present invention in which lithotripsy treatment system 400 comprises laser source 402 and two-channel catheter to 418 through which, optical fiber 404 and tube 416 for cooling liquid injection are inserted. Optical fiber 404 and cooling liquid injection tube 416 are positioned near to stone 406, which is to be fractured. Once in position, proximal end of optical fiber 404 is connected to laser source 402 and cooling liquid injection tube 416 is connected to a container of cooling liquid, for example, a syringe or a serum bag. Cooling liquid is then flushed into the area surrounding stone/hard substance 406 to create immersion/covering medium 408 around it. Immediately after or simultaneously, radiation from laser source 402 is conveyed by optical fiber 404 to the treatment site. Cooling liquid is supplied to the impact site to further reduce thermal heating of the stone, thus diminishing risks of tissue damage caused by stone fragment anchorage and thermal energy. Laser device 402 emits preferably at a wavelength which is highly absorbed in the delivered liquid, thus enhancing evaporation and cavitation effects that lead to efficient stone destruction.

Figure 5:
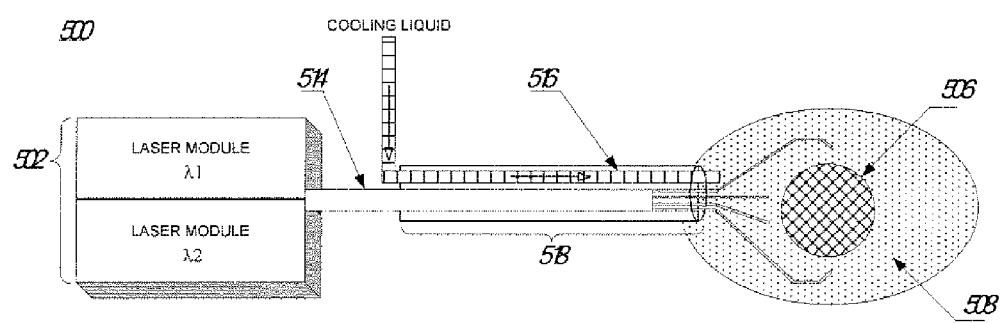
FIG. 5 depicts a diagram of a preferred embodiment of the present invention where a lithotripsy treatment device comprises a laser source, one or more optical fibers and a liquid delivery system.

FIG. 5 depicts another preferred embodiment of lithotripsy treatment system 500 comprising laser source 502 with a two-channel catheter 518 through which, optical fiber set 514 emitting at two wavelengths $\lambda_1$ and $\lambda_2$ or more, and tube 516 for cooling liquid injection are inserted. This embodiment gathers all the advantageous features mentioned in previous embodiments, namely, multiple optical fibers to surround target stone/hard substance 506, two emitting wavelengths, $\lambda_1$ and $\lambda_2$ or more to achieve optimal results and a liquid delivery system 516 for diminishing risks of tissue damage.

EXAMPLE 1

A 1470 nm diode laser source with a 400 μm fiber was used for lithotripsy of calcium oxalate, uric acid and cystine urinary stones. Pulsed radiation was used at high peak power to achieve focused high intensity energy converted into mechanical energy in the form of a cavitation bubble associated with the occurrence of shock-waves. This mechanical energy is responsible for the destruction of calculi. Good lithotripsy was achieved with a power of 20 W and a pulse consisting of power ON 1.0 sec and power OFF 0.3 sec.

Table I shows the results of trials performed in-vitro with a 1470 nm diode laser. The power threshold for achieving plasma formation was measured on fiber tips for different types of fibers.

TABLE I

Plasma formation power thresholds

| FIBER | THRESHOLD |
| --- | --- |
| 1000 μm with flat tip | 3 W |
| 1000 μm with conical tip | 4 W |
| 600 μm side firing | 3 W |
| 600 μm flat tip | 2 W |
| 400 μm flat tip | 1 W |

EXAMPLE 2

Wavelengths of 1470 nm and 1940 nm, are highly absorbed in water; these radiations produce high energy bubbles at fiber tip with photothermal and cavitation effect. With this in mind, in vitro experimentation was carried out using a diode source emitting at a wavelength combination of 1470 nm and 1940 nm with fiber tips immersed in water with continuous wave radiation, in order to try achieving urinary calculi fragmentation. Experimentation produced photothermal bubbles that we named "sparkler-less or sparkless plasma bubbles" at fiber tips, able to produce destruction of urinary stones and also ablation of soft tissue in endourology. Calculus was destroyed without a substantial heat increase in the surrounding water. Total destruction of urinary stones of medium hardness, and significant erosion of cystine stones was obtained.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A laser system for the destruction and removal of kidney stones, calculi, etc. (hard substances) from a urinary tract, by a minimally invasive procedure comprising:
a laser, at least one optical fiber, a component insertable in the urinary tract;
the component configured for disposing the at least one optical fiber being inside the component:
and a fluid delivery subcomponent delivering a fluid medium to surround said hard substance prior to lasing;
wherein said laser emits at least one wavelength that is highly absorbed in the fluid medium surrounding said hard substances.

2. The laser system, according to claim 1, wherein said laser emits in a continuous wave mode.

3. The laser system, according to claim 1, wherein said laser is a diode laser, operating at about either 980±60 nm, 1470±60 nm, or 1940±60 nm.

4. The laser system, according to claim 1, wherein said at least one optical fiber has a concentric core structure, wherein one laser wavelength travels in an inner core and a second wavelength is transmitted in an outer core.

5. The laser system according to claim 4, wherein at least two of the preferred wavelengths are employed in combination: 980 nm and 1470 nm; 980 nm and 1940 nm or 1470 nm and 1940 nm.

6. The laser system according to claim 1, wherein one laser is a fiber laser and a second laser is a pump laser for said fiber laser, and wherein beams from both lasers are transmitted by said at least one optical fiber.

7. The laser system, according to claim 6, wherein said at least one optical fiber has a concentric core structure, wherein said fiber laser wavelength travels in an inner core and a pump laser wavelength is transmitted in an outer core.

8. The laser system according to claim 6, wherein said fiber laser emits at about 1550 nm, and said pump laser emits at either about 915-980 nm or at about 1480 nm.

9. The laser system, according to claim 1, wherein multiple optical fibers are employed, arranged around said target hard substance to speed up its destruction.

10. The laser system according to claim 6, wherein multiple optical fibers are employed, arranged around said target hard substance to speed up its destruction.

11. The laser system according to claim 1, wherein said fluid delivery subcomponent is used to provide a cooling fluid to a treatment site.

12. A minimally invasive method for laser lithotripsy, destruction and removal of kidney stones, calculi, etc. (hard substances), using a laser system, the method comprising:
delivering a fluid medium to surround a hard substance prior to lasing;
delivering laser radiation to the fluid medium surrounding the hard substance; the laser radiation being absorbed the fluid medium; thereby creating sparkless plasma bubbles which destroy hard substance obstructions in a urinary tract in a fast, safe, efficient manner.

13. The method for laser lithotripsy, according to claim 12, wherein a cooling fluid is aimed at a target hard substance to reduce danger of tissue damage from thermal energy or severe fragmentation/anchorage of destroyed obstructions.

* * * * *